(12) United States Patent
Chan et al.

(10) Patent No.: US 10,197,479 B1
(45) Date of Patent: *Feb. 5, 2019

(54) IN VITRO HOMOGENOUS DNA AND RNA CELL BLOCKS MADE USING A MULTI-CHAMBERED ROTATING APPARATUS

(71) Applicant: Alamak Biosciences Incorporation Company Limited, Ma On Shan (HK)

(72) Inventors: Pokman Chan, Salem, MA (US); James Wang, Salem, MA (US); Hok-Yu Chan, New Territories (HK)

(73) Assignee: Alamak Biosciences Incorporation Company Limited, Ma On Shan (HK)

( * ) Notice: Subject to any disclaimer, the term of this patent is extended or adjusted under 35 U.S.C. 154(b) by 50 days.

This patent is subject to a terminal disclaimer.

(21) Appl. No.: 15/186,536

(22) Filed: Jun. 19, 2016

Related U.S. Application Data

(60) Continuation-in-part of application No. 15/178,205, filed on Jun. 9, 2016, and a continuation-in-part of
(Continued)

(51) Int. Cl.
*G01N 1/30* (2006.01)
*G01N 1/36* (2006.01)
*C12Q 1/6876* (2018.01)

(52) U.S. Cl.
CPC ............ *G01N 1/36* (2013.01); *C12Q 1/6876* (2013.01); *G01N 1/30* (2013.01);
(Continued)

(58) Field of Classification Search
None
See application file for complete search history.

(56) References Cited

U.S. PATENT DOCUMENTS 5,457,050 A 10/1995 Mazurek
6,913,921 B2 7/2005 Fischer
(Continued)

FOREIGN PATENT DOCUMENTS

EP 1642131 B1 10/2008
WO WO2004077057 9/2004
(Continued)

OTHER PUBLICATIONS

ASC—Applied StemCells Genome Editing in Vitro and in Vivo—website URL www.appliedstemcell.com.
(Continued)

*Primary Examiner* — Suchira Pande
(74) *Attorney, Agent, or Firm* — Carrie Stroup

(57) ABSTRACT

Homogenous DNA or RNA cell blocks used as a standard and comprising uniformly distributed cells, or ratio of cells, for use as a positive control for a biomarker in immunohistochemistry slide scanning and image analysis. The cell blocks are made using a Homogenous Cell Mixture (HCM) apparatus comprising a rotating multi-tiers that de-clump and filter single cells downward to mix with a fixation liquid-3% agarose. The uniform rotation of the tiers is under the operational control of a motorized mechanism, and results in a cell mixture comprising a constant density of cells, which is then transferred into molds to make formalin fixed paraffin embedded (FFPE) cell blocks. The size of the molds is also determined based upon a computation that factors in the total number of cells (e.g. density) in a cell block that a user desires, and the total cell volume for a specific cell type selected.

20 Claims, 9 Drawing Sheets

Related U.S. Application Data application No. 15/178,103, filed on Jun. 9, 2016, now Pat. No. 10,132,729, and a continuation-in-part of application No. 13/801,617, filed on Mar. 13, 2013, now Pat. No. 9,395,283, application No. 15/178,205, which is a division of application No. 13/801,617, filed on Mar. 13, 2013, now Pat. No. 9,395,283, application No. 15/178,103, which is a division of application No. 13/801,617, filed on Mar. 13, 2013, now Pat. No. 9,395,283.

(60) Provisional application No. 61/610,556, filed on Mar. 14, 2012.

(52) U.S. Cl.
CPC . *C12Q 2600/166* (2013.01); *G01N 2001/302* (2013.01); *G01N 2001/366* (2013.01); *G01N 2001/368* (2013.01)

(56) References Cited

U.S. PATENT DOCUMENTS

| | | | |
|---|---|---|---|
| 7,541,161 | B2 | 6/2009 | Fischer |
| 9,097,618 | B2 | 8/2015 | Barker et al. |
| 9,395,283 | B1 | 7/2016 | Chan et al. |
| 9,909,964 | B2 * | 3/2018 | Boonyaratanakornkit et al. ......... C12Q 1/06 |
| 2003/0157523 | A1 * | 8/2003 | Frantz ............... G01N 1/36 506/23 |
| 2006/0154234 | A1 | 7/2006 | Winther et al. |
| 2007/0037138 | A1 | 2/2007 | Winther |
| 2007/0218542 | A1 | 9/2007 | Li et al. |
| 2008/0082351 | A1 | 4/2008 | Kelley-Hrabe et al. |
| 2011/0306064 | A1 | 12/2011 | Taylor et al. |
| 2012/0088233 | A1 | 4/2012 | Boonyaratanakornkit et al. |
| 2013/0183710 | A1 | 7/2013 | Reifenberger et al. |
| 2014/0335533 | A1 | 11/2014 | Boonyaratanakornkit et al. |

FOREIGN PATENT DOCUMENTS

| | | |
|---|---|---|
| WO | WO2005003773 A1 | 1/2005 |
| WO | WO2012051332 A1 | 4/2012 |
| WO | WO2016010858 A1 | 1/2016 |

OTHER PUBLICATIONS

Office Action dated Sep. 28, 2015 in connection with U.S. Appl. No. 13/801,617.

Office Action dated Mar. 21, 2016 in connection with U.S. Appl. No. 13/801,617.

Koch et al., "Real-time Quantitative RT-PCR Shows Variable, Assay-dependent Sensitivity to Formalin Fixation: Implications for Direct Comparison of Transcript Levels in Paraffin-embedded Tissues", Diagn Mol Pathol. (2006) vol. 15:149-156.

Shi et al., "DNA Extraction from Archival Formalin-fixed, Paraffin-embedded Tissue Section Based on the Antigen Retrieval Principle: Heating Under the Influence of pH", J. Histochem Cytochem. (2002) vol. 50: 1005-1011.

U.S. Appl. No. 13/801,617 of Chan, P. filed Mar. 13, 2013.

U.S. Appl. No. 15/178,205 of Chan, P. filed Jun. 9, 2016.

U.S. Appl. No. 15/178,103 of Chan, P. filed Jun. 9, 2016.

Office Action dated Dec. 12, 2017 in connection with U.S. Appl. No. 15/178,103.

Office Action dated Dec. 26, 2017 in connection with U.S. Appl. No. 15/178,205.

Alamak Biosciences, slide presentation entitled "Seeing is Believing Seeing is Deceiving Towards a Standardization of Histology in Biomarker Qualification".

\* cited by examiner

Cell block paraffin processing schedule- steps

| Steps | Medium | Time | Temperature |
|---|---|---|---|
| 1 | 70% EtOH | 2 Hours | RT |
| 2 | 70% EtOH | 2 Hours | RT |
| 3 | 70% EtOH | 2 Hours | RT |
| 4 | 80% EtOH | 2 Hours | RT |
| 5 | 80% EtOH | 2 Hours | RT |
| 6 | 95% EtOH | 2 Hours | RT |
| 7 | 95% EtOH | 2 Hours | RT |
| 8 | 100% EtOH | 2 Hours | RT |
| 9 | 100% EtOH | 2 Hours | RT |
| 10 | 100% EtOH | 2 Hours | RT |
| 11 | Slide Brite | 2 Hours | RT |
| 12 | Slide Brite | 2 Hours | RT |
| 13 | Slide Brite | 2 Hours | RT |
| 14 | Paraffin | 2 Hours | 56°C Oven |
| 15 | Paraffin | 2 Hours | 56°C Oven |
| 16 | Paraffin | 2 Hours | 56°C Oven |

FIG. 3

| Steps and Solution | Time |
|---|---|
| Xylene | 5 Minutes |
| Xylene | 5 Minutes |
| Xylene | 5 Minutes |
| 100% EtOH | 5 Minutes |
| 100% EtOH | 5 Minutes |
| 100% EtOH | 5 Minutes |
| 95% EtOH | 5 Minutes |
| 95% EtOH | 5 Minutes |
| 80% EtOH | 5 Minutes |
| 80% EtOH | 5 Minutes |
| 70% EtOH | 5 Minutes |
| 70% EtOH | 5 Minutes |
| ddH2O | 5 Minutes |
| ddH2O | 5 Minutes |
| Hematoxylin | 30 Seconds |
| Running Tap Water | 5 Minutes |
| Scott's Bluing Solution | 30 Seconds |
| Running Tap Water | 5 Minutes |
| ddH2O | 5 Minutes |
| 70% EtOH | 5 Minutes |
| 70% EtOH | 5 Minutes |
| 80% EtOH | 5 Minutes |
| 80% EtOH | 5 Minutes |
| 95% EtOH | 5 Minutes |
| 95% EtOH | 5 Minutes |
| 100% EtOH | 5 Minutes |
| 100% EtOH | 5 Minutes |
| Xylene | 5 Minutes |
| Xylene | 5 Minutes |

FIG 4

| Cell Block Cut Slice Number | Number of Cells per slice | Amount of DNA per Slice |
|---|---|---|
| Slice Number 1 | 839 | 4.41ng |
| Slice Number 101 | 817 | 4.12ng |
| Slice Number 201 | 832 | 4.22ng |
| Slice Number 301 | 842 | 4.29ng |
| Slice Number 401 | 836 | 4.31ng |
| Slice Number 501 | 819 | 4.17ng |
| Slice Number 601 | 822 | 4.21ng |
| Slice Number 701 | 836 | 4.11ng |
| Slice Number 801 | 845 | 4.47ng |
| Slice Number 901 | 827 | 4.16ng |
| Slice Number 1001 | 815 | 4.02ng |

FIG. 7A

| Cell Block Cut Slice Number | Number of Cells per slice | Amount of RNA per Slice |
|---|---|---|
| Slice Number 1 | 1002 | 19.8ng |
| Slice Number 101 | 1089 | 21.2ng |
| Slice Number 201 | 1052 | 22.7ng |
| Slice Number 301 | 1077 | 21.9ng |
| Slice Number 401 | 1023 | 22.5ng |
| Slice Number 501 | 1053 | 23.1ng |
| Slice Number 601 | 1066 | 22.8ng |
| Slice Number 701 | 1027 | 21.5ng |
| Slice Number 801 | 1078 | 22.6ng |
| Slice Number 901 | 1059 | 21.9ng |
| Slice Number 1001 | 1062 | 22.7ng |

FIG. 7B

IN VITRO HOMOGENOUS DNA AND RNA CELL BLOCKS MADE USING A MULTI-CHAMBERED ROTATING APPARATUS

CROSS-REFERENCE TO RELATED APPLICATIONS

This application is a continuation-in-part of and claims priority to U.S. Ser. No. 13/801,617 filed Mar. 13, 2013, issued as U.S. Pat. No. 9,395,283, which claims priority to Provisional U.S. Patent Application Ser. No. 61/610,556 filed Mar. 14, 2012.

This application is also a continuation-in-part of and claims priority to U.S. Ser. No. 15/178,103 filed on Jun. 9, 2016, which is a divisional of U.S. Ser. No. 13/801,617 filed Mar. 13, 2013, issued as U.S. Pat. No. 9,395,283, which claims priority to Provisional U.S. Patent Application Ser. No. 61/610,556 filed Mar. 14, 2012.

This application is a continuation-in-part of and claims priority to U.S. Ser. No. 15/178,205 filed on Jun. 9, 2016, which is a divisional of U.S. Ser. No. 13/801,617 filed Mar. 13, 2013, issued as U.S. Pat. No. 9,395,283, which claims priority to Provisional U.S. Patent Application Ser. No. 61/610,556 filed Mar. 14, 2012, the contents of all which are incorporated herein by reference in their entirety.

COPYRIGHT NOTICE

A portion of the disclosure of this provisional patent application document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

TRADEMARKS DISCLAIMER

The product names used in this document are for identification purposes only. All trademarks and registered trademarks are the property of their respective owners.

FIELD OF THE INVENTION

The present invention pertains to an apparatus, and its use in methods for embedding cellular materials within a formalin fixed paraffin substrate to create a homogenous cell block of evenly distributed cell densities for use as a standard in immunohistochemistry experiments.

BACKGROUND OF THE INVENTION

Immunohistochemistry (IHC) and in situ hybridization (ISH) are in vitro laboratory procedures used to detect and diagnose abnormal conditions, such as cancer. IHC requires detecting proteins in cells of tissue section by hybridizing antibodies to antigens, while ISH hybridizes radio-labelled complementary DNA/RNA probe to DNA/RNA within a tissue. The procedures are also widely used in basic research to understand the distribution and localization of biomarkers and differentially expressed proteins/DNA/RNA in different parts of a biological tissue.

According to the FDA Draft "Guidance for Industry Use of Histology in Biomarker Qualification Studies", released December 2011, a biomarker is defined as: "a characteristic that is objectively measured and evaluated as an indicator of normal biologic processes, pathogenic processes, or biological responses to a therapeutic intervention.". The report goes on to state that "a poorly characterized biomarker can do considerable harm. A poorly characterized biomarker may lead to inappropriate removal of a drug from development, encourage development of a drug that is unlikely to be approved, or lead to an erroneous perception of safety.".

Positive and negative experimental controls for IHC and ISH are created from archived tissue blocks, or from cell lines embedded in tissue medium (i.e. formalin fixed paraffin embedded-FFPE). A positive control comprises a tissue or cell block containing the biomarker (antigen/DNA/RNA) of interest. Cell lines or purified cell from tissues or blood samples of affected patients are a valuable tool to provide known positive controls. These cells can provide a homogeneous tissue in a desirable amount, and properties can be controlled by molecular, cytogenetic and biochemical characteristics. Cells created in a paraffin block can provide sections for studying ex-vivo cell cycles, signaling pathways, and activation-dependent effects with biochemical agents. Cells grown in culture can be cytospun or prepared as cell smears on glass slides, however, these conditions are quite different from tissue blocks that have been fixed, dehydrated and embedded in paraffin.

Cell pellets fixed in formalin become very tough, therefore embedding the pellet into paraffin creates a pellet with very dense cells. It is difficult to create cell blocks that serve as positive controls that are of a uniform density because of the clumping of the cells. And, without uniform density, cell block staining, image scanning and analysis may be inconsistent.

The current invention solves this problem by creating a "homogeneous" cell block possessing superior homogeneity of cells that are evenly distributed within each section cut from the cell block. The sections are then useable as a control standard.

The lack of reliable controls in IHC/ISH studies is a recognized problem. For example, it was recently noted that "... IHC as a platform for biomarkers has been challenged by more quantitative molecular assays with reference standards but that lack morphologic context". For IHC to be considered a "top-tier" biomarker assay, it must provide truly quantitative data on par with non-morphologic assays, which means it needs to be run with reference standards. Until pathologists can run immunohistochemical assays with known controls that serve as true reference standards, the use of IHC on histologic sections will be considered a less valued or preliminary method of defining a biomarker" (Dunstan et al, *Toxicologic Pathology*, 39: 988-1002, 2011).

Therefore, there is a need within the medical and research industries, to produce reliable controls, such as a cell block of uniformly distributed cells, or ratio of cells, for use as a positive control for a biomarker in immunohistochemistry slide scanning and image analysis.

SUMMARY OF THE INVENTION

The present invention encompasses an in vitro tissue technology method, and a multi-chambered-tiered Homogenous Cell Mixture (HCM) apparatus, for creating a cell block comprising a homogenous mixture of cells for use as a molecular pathology standard and tissue based biomarker standard. The present invention also comprises a solid composition (i.e. cell block) of homogenous cells produced via this method and the HCM apparatus, such as formalin fixed paraffin embedded (FFPE) cells, and a method of use of this HCM apparatus derived composition/block as a control or standard in immunohistochemistry studies. Slices from the solid composition are imaged, and the DNA or RNA content is quantified within one or more slices via methods well known in the art.

The HCM apparatus of the present invention is a non-obvious improvement of the apparatus disclosed in FIG. 2, of U.S. Ser. No. 13/801,617 filed Mar. 13, 2013, from which this patent application depends. The HCM apparatus comprises multiple components to facilitate the even distribution of cells as they fall vertically downward through the apparatus, from tier-to-tier, and with all three chambers-tiers rotating at the same speed (i.e. rotational or angular velocity) under the operational control of a motorized mechanism. Additionally, the bottom surface of the top tier comprises evenly spaced holes for the cells to fall through onto the second tier. The top tier of the HCM apparatus is interchangeable, and is selected based upon the diameter of the holes. The diameter of the holes is customized to be slightly larger than the diameter of a specific type of cell to allow single cells to fall through the holes, but not clumps of cells.

The second tier further comprises two vertically aligned rotating wheels comprising a plurality of horizontally aligned cell strainers (or meshes, or bottom surfaces comprising a plurality of evenly spaced holes of a pre-selected diameter or size). The top wheel further strains the cells falling downward from the top tier to ensure that they are single cells. The proximal end of an open-ended tube extends between the first, top wheel and second, bottom wheel in order to pour, or inject, a liquid (e.g. agarose) onto the cells to create a mixture of cells. The proximal end of the tube further comprises evenly spaced holes to inject the fluid downward onto the second wheel at a constant rate and volume throughout the radius of the wheel to ensure a "homogenous" mixture of cells, which then drains through the strainer, mesh, or holes of the second wheel and into the apparatus's bottom chamber. The homogenous cell mixture is then transferred from the bottom chamber (e.g. poured) into a mold (A) of a pre-computed size and/or volume per the mathematical calculations disclosed herein.

The present method of making a cell block permits the mixing of different types of cells and/or the same types of cells with a pre-determined and precise mixture/ratio as required for tissue based biomarker standards.

The cell composition/block contains cells in a "homogeneous" state, meaning the cells are evenly distributed within the whole cell block while a minimal number of large clumps are present. The "homogenous" stage also means that a certain defined percentage or number or ratio of cells within the composition/block are all evenly distributed. For example, the cell block may contain 50% cell A and 50% cell B, wherein it remains this ratio of homogeneity throughout the whole cell composition/block (length, width, thickness) such that each slice or cross-section of the composition/block will comprise an evenly distributed number of 50% Cell A/50% Cell B ratio along the radius or diameter, and along the thickness of the slice. The ratio of cells may be defined with: 1) different types of cells; 2) different combinations of certain designated percentages of each cell type; 3) cells having undergone different treatment protocols (such as of a biological process, chemicals, drugs, radiations, and/or temperature); and, 4) cells with different genetic modifications such as mutations, insertion of gene(s). Therefore, these types (1-4) of mixture of cells are built into the blocks with the designated ratios.

The cell mixture within the composition/block may also comprise the following: a mixture of the same type of cell with different genetic modifications; a mixture of the same type of cell with different protein, gene, or nucleic acids (DNA, RNA) expression; and a mixture of different types of cells with different genetic backgrounds, and/or with different levels of expression of DNA, RNA, gene and/or proteins.

The homogeneous cell composition/block of the present invention further comprises the properties that the block may be scanned while in a fresh stage, cut with any kind of cutting device, and with or without changing its temperature. The cell block can also be processed to formalin fixed paraffin embedded (FFPE) and cut as FFPE section utilizing any cutting device not limited to a rotator microtome, sliding microtome and any other cutting methods. It is noted, though, that other non-FFPE homogenous cell blocks may be produced by the method of the present invention.

The method of use of the homogeneous cell block (i.e. FFPE and non-FFPE) produced by utilizing the HCM apparatus of the present invention is to utilize sections of the cell block as a biomarker standard for any tissue based biomarker study, as well as biomarker analysis using molecular biology methods such as polymerase chain reaction (PCR), sequencing, and microarrays. The FFPE cell section with defined number of cells with defined ratio/mixture percentage is used as a standard for sensitivity and specificity evaluation histology based biomarker studies run using either machines or manual operation methods.

The detection of homogeneity can be performed using cell counting of the same type of cell or different types of cells presents in the section. Cell counting methods are well known in the art, such as by digital immunohistochemistry devices (e.g. Aperio® ScanoScope). Detection of homogeneity can also be confirmed by the extraction and quantification of nucleic acids from each cell block section to determine the amount of nucleic acids in each block and the ratio of a mixture of cells within the block. Methods of DNA (polynucleotide) and RNA (ribonucleic acid) extraction and quantification are well known in the art.

The method of making the cell composition comprises the following steps: step 1—determine mold volume for a specific cell type(s) and/or a desired density of cells within a cell block using the equations disclosed herein; step 2—pre-treatment of cells for cell block preparation; step 3—cell block preparation; step 4—sectioning cell blocks and hematoxylin staining; step 5—DNA or RNA extraction; and step 6—DNA or RNA quantitation.

Step 1—the determination of the mold volume: the total volume of the cell mold is generally computed by dividing the total volume of the affected and normal cells, summed together, by the volume of the percent of agarose (1-3%) used in the fixation liquid within the HCM apparatus.

Step 2—pre-treatment of cells: a) determine or select a range of the total number, or ratio of different cell types (e.g. control versus cancerous), or density of cells in the cell block. The density of the cells within the final composition/block is controlled by adjusting the size of the mold in order to produce cell sections of a certain number/density/count, wherein each section, or slice cross-sectional area, contains a particular number of cells within a certain defined limit. The size of the mold is determined via a complicated mathematical computation disclosed herein. This method produces cell blocks of a certain size (e.g. volume, area, length and radius, etc.) to control the number of cells in each block in order to produce a section (slice) comprising an evenly distributed number or ratio of cells (i.e. pre-designated number). Therefore, each section or slice, which comprises a cell-block cross-section, contains a particular number of cells within a certain defined limit, or range, that is selected before the method of making the cell block starts (i.e. before step 1—pretreatment of cells).

Step 2 then comprises: a) passing cells through a cell collection device, such as the top tier of the HCM apparatus (e.g. FIGS. 2A-2C, 210), and while the cells are in suspension, fixed pellet, or unfixed pellet form; b) performing cell counting and cell viability; c) fixing the cells in a composition comprising paraformaldehyde in PBS to create a cell pellet; and d) immobilizing the suspension at a controlled temperature for later use in step 3.

Step 3—cell block preparation: basically comprises: a) passing cells through the entire HCM apparatus to create a homogenous mixture of immobilized cells; b) injecting the cell mixture into a Mold A (first mold), set, and remove from the Mold A; and, c) processing cell blocks with paraffin, removing individual blocks from paraffin, and embedding into a Mold B (second mold).

Step 3(*a*) further comprises passing the cells or cell pellets through the entire HCM apparatus, which comprises a clean top chamber-tier (FIGS. 2A-2C, 210). The cells are immobilized in the suspension, or mixture, after mixing with the liquid (e.g. agarose) that is injected from the open-ended tube into the second tier of the HCM apparatus. In step 3(*b*), the cell mixture is then injected into a first mold (i.e. Mold A), which is of a pre-determined size and volume as computed from the computation in step 1, to solidify as a "homogenous cell block". After setting, the cell block is processed for paraffin, and embedded into a second mold (i.e. Mold B) which is also of a pre-determined size and volume as determined from the computation in step 1.

Step 4—sectioning cell blocks: comprises cutting along the cross-section of the homogenous cell block that is removed from Mold B. Each section cut is about 10 μm in thickness, and undergoes hematoxylin staining. The thickness of the section/slices may also be other sizes, such as 5 μm.

Step 5—performing DNA or RNA extraction from one or more cell sections by methods well known in the art.

Step 6—performing DNA or RNA quantification, by methods well known in the art, of the extracted DNA/RNA of step 5 to demonstrate cell block homogeneity.

The HCM multi-chambered-tiered apparatus in steps 2 and 3 further comprises: a rotating circular upper cell containing chamber (FIG. 2A, item 210) able to pass the pre-treated cells downward onto a circular rotating middle secondary chamber; a circular rotating middle secondary chamber 218 comprising an upper wheel (FIG. 2A, item 220) and a lower wheel (FIG. 2A, item 224) able to pass the pre-treated cells downward through to a lower cell collection chamber (FIG. 2A, item 230), and an open-ended tube (FIG. 2A, item 250) able to simultaneously inject the fluid to create a homogenous cell mixture. Furthermore, the open-ended tube is positioned between the upper chamber and the lower chamber to inject liquid comprising a fixation solution of a specific volume (e.g. 1-3% agarose) that is determined by the type of cells; and the open end of the tube comprises a plurality of holes evenly spaced (FIG. 2A, 252) to inject the fluid in a downward pattern for even distribution along the radius of the wheel. The apparatus is also under the operational control of a motorized mechanism to rotate the upper, lower, and middle chambers in unison. The apparatus further comprises a transparent, hollow cylinder that encases the middle and lower chambers and the proximal end of the open-ended tube so as to prevent contamination of the pre-treated cells.

The various embodiments of the present disclosure further comprise: a solid composition, such as an FFPE cell block, that is produced using the multi-chambered-tiered apparatus disclosed herein. The solid composition is suitable for use as a standard, otherwise known herein as a positive experimental control. The solid composition comprises a mixture of cells within a formalin fixed paraffin embedded (FFPE) tissue, wherein the cells are evenly distributed throughout the composition, and are of a pre-determined number (i.e. cell count). Within the solid composition, the mixture of cells may comprise: a ratio of different types of cells; a different combination of certain percentages of each cell type; and/or the same type of cells exposed to different treatment protocols; and, wherein the ratio of the mixture of cells is evenly distributed within the composition. And the ratio of the mixture of cells can be determined within each cross-section of the composition by conducting cell counting, and/or DNA or RNA extraction and quantification. And within the solid composition, the mixture of cells may comprise: the same type of cells with different genetic modifications; the same type of cells with different protein or DNA or RNA expression; different types of cells with different genetic backgrounds; and/or different types of cells with different gene/protein expression levels.

The various embodiments of the present disclosure further comprise: a solid composition, and a method of making the solid composition, by using the multi-chambered-tiered apparatus of the present disclosure. The steps comprise: a) passing a plurality of pre-treated cells vertically through holes in the multi-chambered-tiered apparatus and mixing the pre-treated cells with a fluid simultaneously to create a homogenous cell mixture of immobilized cells; b) injecting the homogenous cell mixture into a first mold, letting the mixture set to immobilize the cell mixture, and removing a solid composition from the first mold; c) processing the solid composition with paraffin, removing the solid composition from the paraffin, and embedding the solid composition into a second mold to produce formalin fixed paraffin embedded (FFPE) cells; and d) removing the solid composition from the second mold, wherein the solid composition comprises a homogenous mixture of formalin fixed paraffin embedded (FFPE) cells with a uniform density of cells throughout the solid composition.

Furthermore, steps (a-d) are preceded by selecting a one or more cell types, and a desired density range, or total cell count, of the selected cells in the solid composition, and determining the volume of the first and second mold based on the diameter of the selected cell types, and the desired density, or total cell count (see FIG. 1, step 1).

And in step (a), the pre-treated cells that are passed through all or part of the multi-chambered-tiered apparatus are in suspension, or in a fixed pellet form, or in an unfixed pellet form. And the process of "pre-treating" the cells comprises the steps of: fixing the cells in paraformaldehyde or formaldehyde, and phosphate buffered saline (PBS), then centrifuging and rinsing the cells. In a particular embodiment, the pre-treatment of cells further comprises: fixing the cells for 24 hours at room temperature with freshly prepared 2% paraformaldehyde in PBS to create a cell pellet; centrifuging the cell pellet; rinsing the cell pellet with 70% ethanol; and, storing the cells at 4 degrees Celsius.

BRIEF DESCRIPTION OF THE DRAWINGS

The in vitro homogenous cell block, methods of making, and methods of use that embody the above and other inventive features will now be described with reference to the following drawings:

FIG. 3 is a table comprising the sequential steps in the Cell Block Paraffin Processing Schedule.

FIG. 4 is a table comprising the sequential steps in Hematoxylin Staining Procedure.

FIG. 7A is a table of the results quantifying the amount DNA in the slices of FIG. 5, and that demonstrates the even distribution of the cells and their DNA throughout the cross-section and length of the cell block.

FIG. 7B is another table of the results from a different cell block than FIG. 7A, that quantifies the total RNA in each slice of FIG. 6, and that demonstrates the even distribution of the cells and their RNA throughout the cross-section and length of the cell block.

DETAILED DESCRIPTION OF AN EXEMPLARY EMBODIMENT

Glossary of Terms

Figure 1:
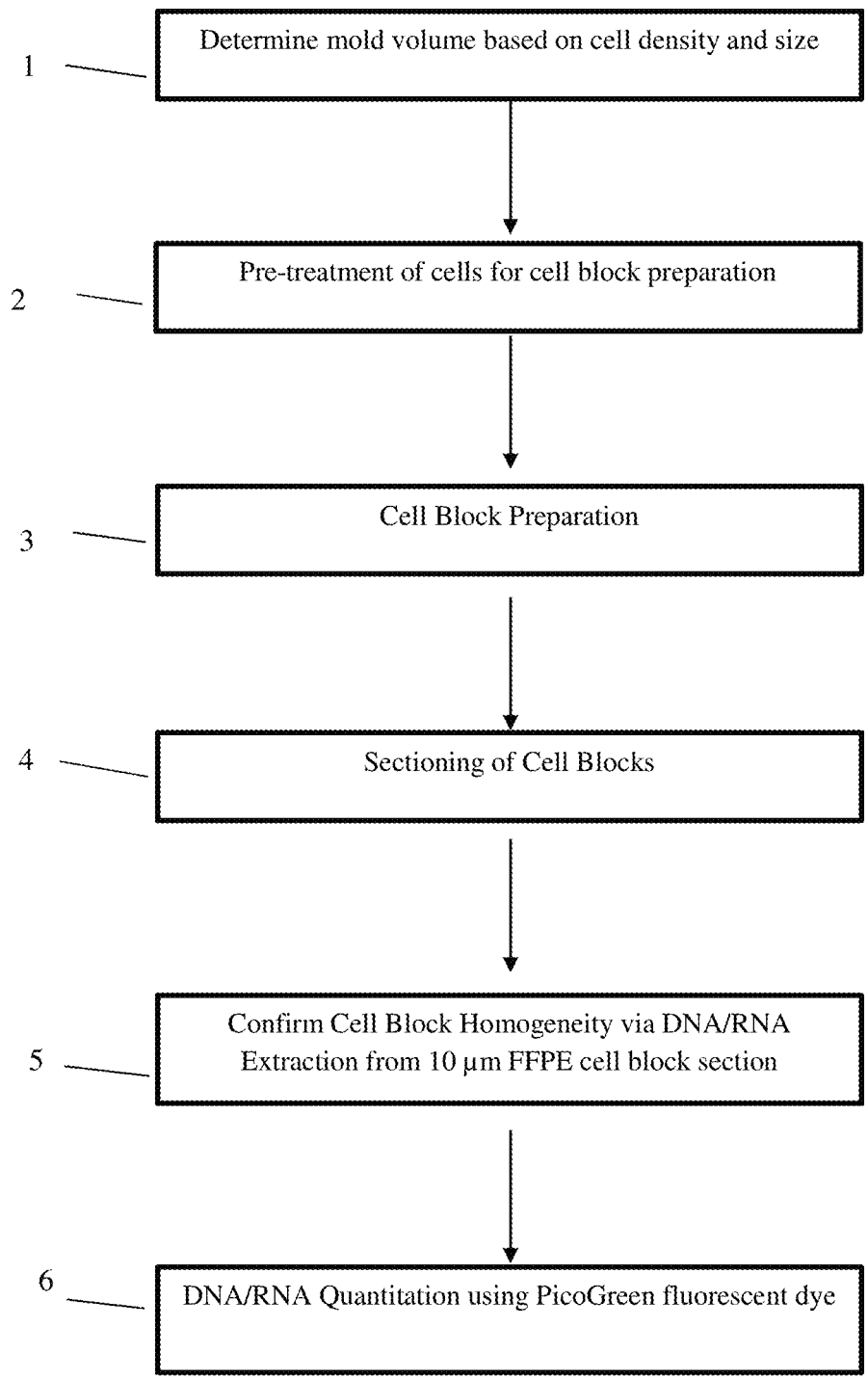
FIG. 1 is a flowchart of steps for preparing in vitro homogenous cell blocks.

As used herein, the term "Homogenous Cell Block" refers to solid composition of one or more types of cells, in which each type of cell is evenly distributed throughout the volume, area, length, radius, etc. of the solid composition in relation to cells of its own cell type, and in relation to cells of a different cell type.

As used herein, the term "Cell Mixture" refers to a liquid, semi-solid, and solid composition comprising one or more cell types.

As used herein, the term "Normal Cells" or "Control Cells" refers to cells that are in their normal healthy state. A homogenous cell block produced by the methods and apparatus of the present disclosure may comprise an even, homogenous distribution of one or more types of normal cells suitable, wherein slices of the cell block are suitable for use as an experimental standard.

As used herein, the term "Affected Cells" or "Positive Control Cells" refers to cells used in steps 1-6 that are known to comprise a trait that is being studied, such as a genetic mutation associated with a particular disorder or disease. Therefore, a homogenous cell block produced by the methods and apparatus of the present disclosure may comprise an even, homogenous distribution of one or more types of affected cells, with or without normal cells of the same type or of a different cell type, wherein slices of the cell block are suitable for use as a positive control, experimental standard.

In the following detailed description of the invention, reference is made to the drawings in which reference numerals refer to like elements, and which are intended to show by way of illustration specific embodiments in which the invention may be practiced. It is understood that other embodiments may be utilized and that structural changes may be made without departing from the scope and spirit of the invention.

Figure 2A:
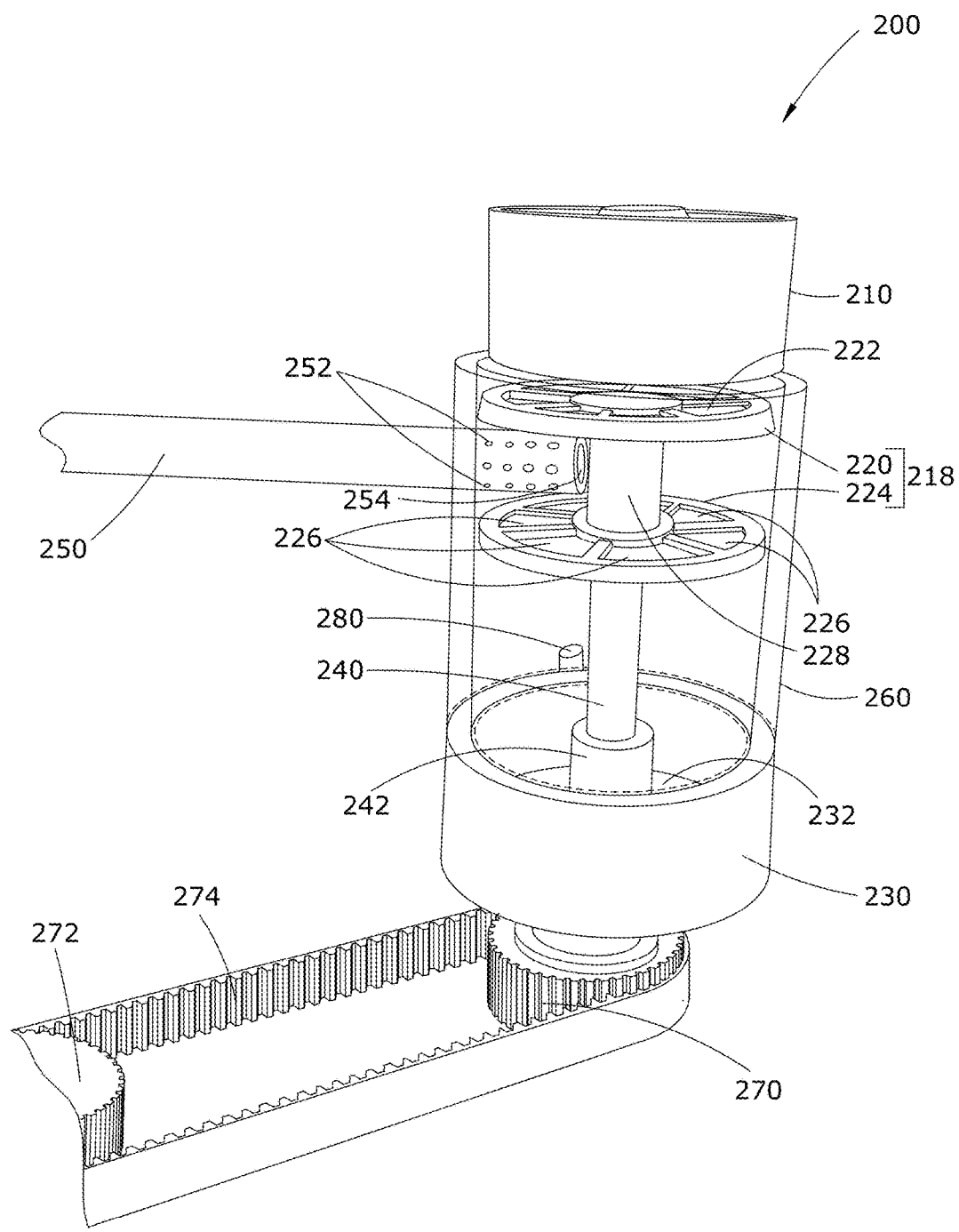
FIG. 2A is front elevational view of the Homogenous Cell Mixture (HCM) apparatus used in the method of preparing the homogenous cell blocks.
Figure 2B:
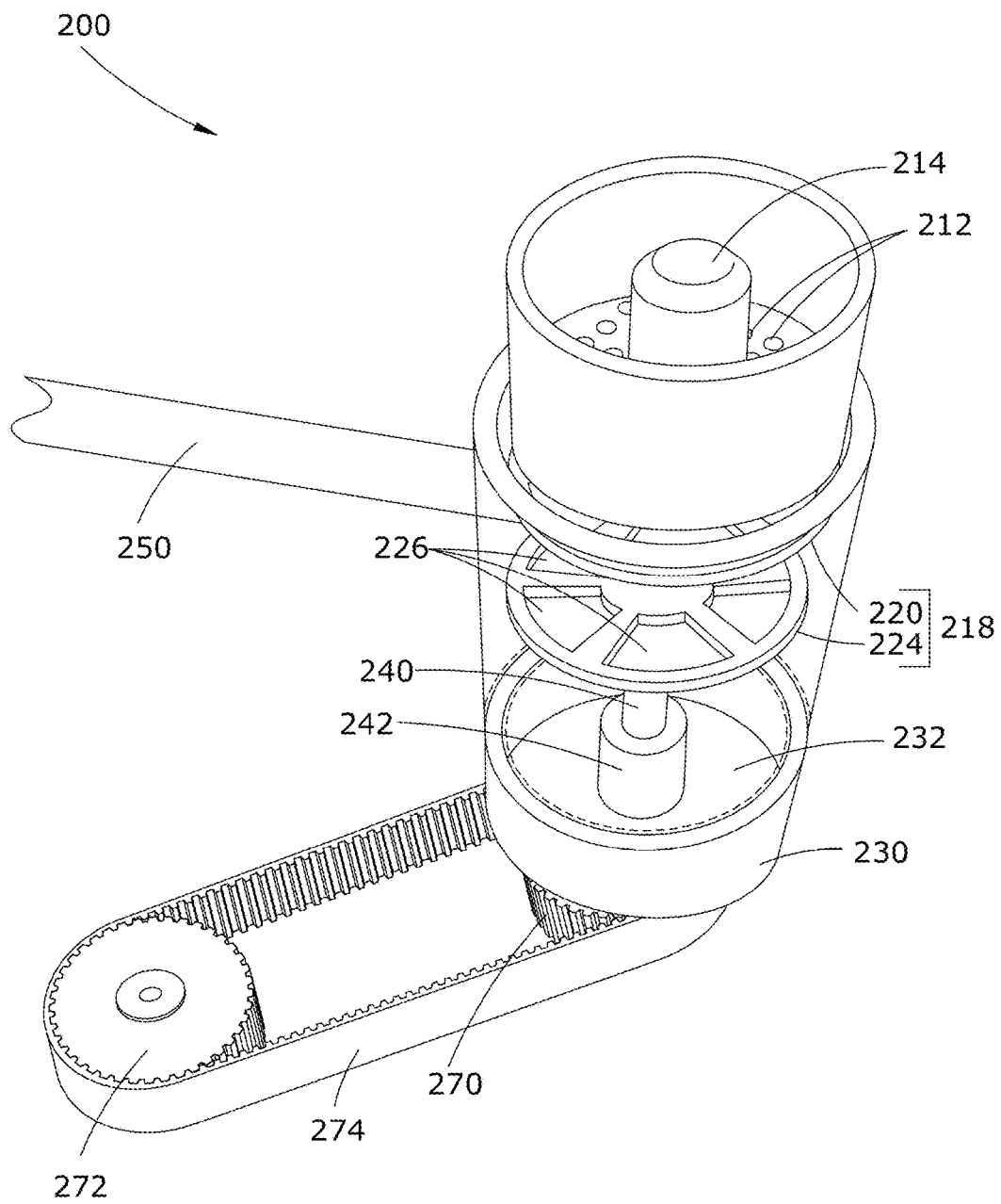
FIG. 2B is a top perspective view of the front of the HCM apparatus.
Figure 2C:
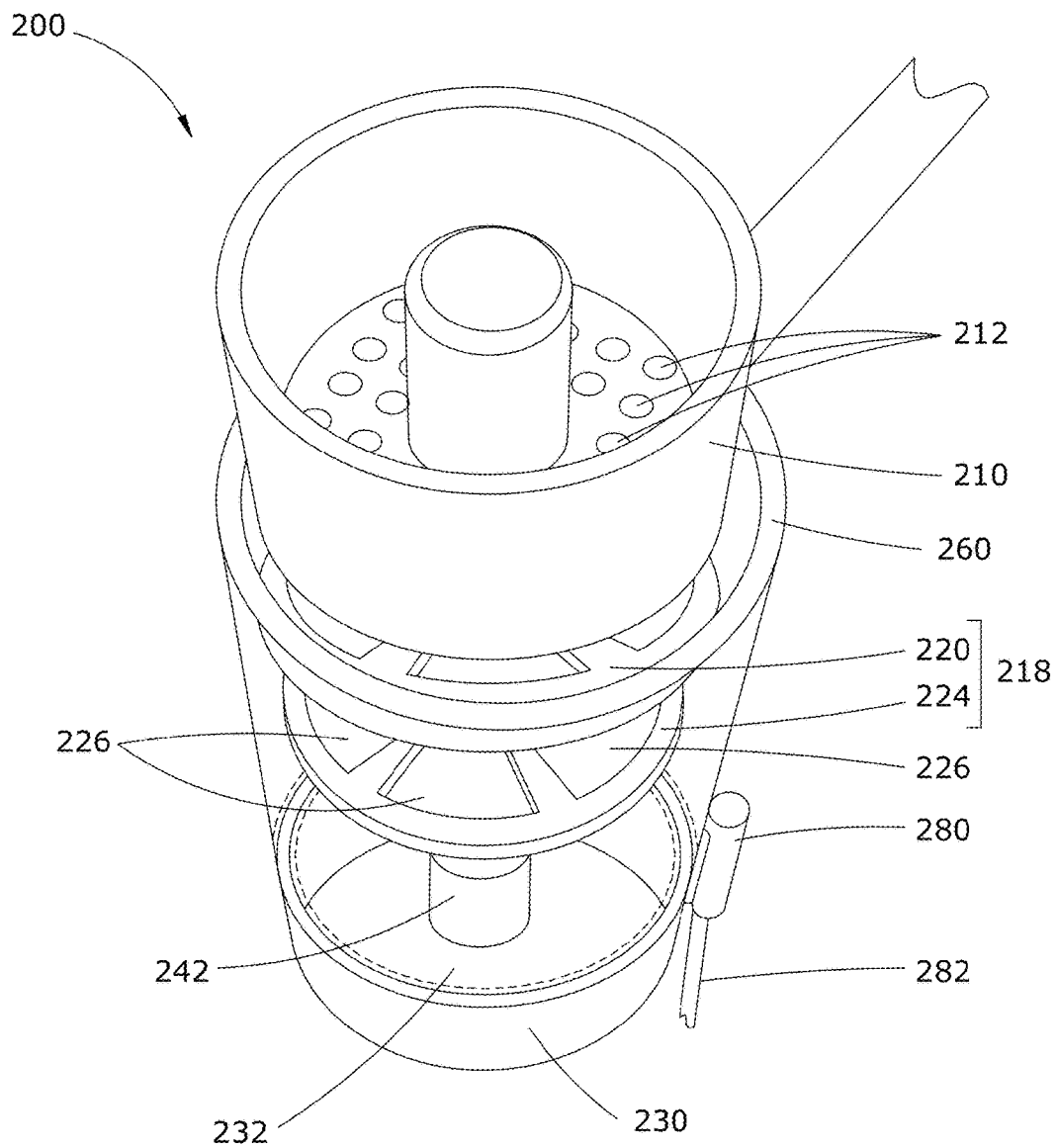
FIG. 2C is a top perspective view of the back of the HCM apparatus.

By way of non-limiting examples, cell mixtures of the present disclosure that are used in the homogenous cell blocks produced via use of the apparatus 200 of FIG. 2A-2C comprises: a pre-determined ratio of different types of cells; different combination of certain percentages of each cell type; and/or the same type of cells exposed to different treatment protocols; and, wherein the ratio of the mixture of cells is evenly distributed within the composition.

Additionally, and also by way of non-limiting examples, the cell mixtures may comprise: the same type of cells with different genetic modifications; the same type of cells with different protein or nucleic acids expression; different types of cells with different genetic backgrounds; and/or, different types of cells with different gene/protein expression levels, and, wherein the ratio of the mixture of cells is evenly distributed within the composition.

As used herein, the term "Specific Volume" refers to the volume occupied by a unit of mass of a material (e.g. units of $m^3/kg$, ml/g). A cell's spherical volume equals its volume (4/3*pi*radius cubed) in relation to its mass, and may be in the units of micrometers**3 ($\mu m^3$)/milligram.

Homogenous Cell Block (HCM) Apparatus

FIGS. 2A-2C illustrate the Homogenous Cell Block (HCM) apparatus 200, which comprises three main vertically aligned tiers: a top circular interchangeable chamber 210; a middle tier 218 comprising two aligned, flat circular wheels 220, 224; and a bottom circular chamber 230 to collect the homogenous cell mixture. Each of the three tiers further comprise a center hole that a rotating bar 240 runs through. Bar 240 is connected on the bottom end to gear 270, which is part of a motorized mechanism to turn bar 240, and hence the three tiers, at the same rotational speed to ensure that the cells and cell mixture fall in an even pattern to the tier below.

The motorized mechanism further comprises gear 272 and belt 274, that in conjunction with gear 270, rotate in the same direction (clockwise or counterclockwise) at a user selected speed. Power sources for small electric devices are well known in the art, especially those utilizing gears and belts. When a power source is directly connected to gear 272 to rotate it, belt 274 will rotate in the same direction as its inner grooves connects with the gear 272 outer grooves, and thus cause gear 270 to rotate as the same belt grooves move from gear 272 to connect with the outer grooves of gear 270, and then back to gear 272. This in turn will cause bar 240, and tiers 210, 218, and 230 to rotate in unison at a constant user's selected speed.

As shown in FIGS. 2B and 2C, the removable top chamber 210 further comprises a plurality of evenly spaced holes 212 in the bottom the chamber that are sized to permit single cells of a specific diameter to fall downward through them, while preventing clumps of cells from passing through the holes. For example, if the control or affected cells have a diameter of 5 µm, the holes 212 will be about 1 µm wider in diameter (i.e. 6 µm).

The top chamber 210 is also interchangeable by removing the center knob (see FIG. 2B, 214) and sliding the chamber 210 off of the center bar 240. The top chamber 210 is replaced when cells of a different diameter, or larger total volume, are being used within a new homogenous cell block. For example, when a larger total volume of cells or total number of cells is being used, then a top chamber 210 is selected that has a higher density or number of holes 212 to expedite the rate at which the cells pass individually downward from the top 210 to the middle chamber 218. The top chamber 210 may also be replaced between steps within the method of making the cell blocks—e.g. swapping out chamber 210 to ensure that the cell mixture is not contaminated when it is passed through apparatus 200 again.

The second, middle tier 218 comprises two vertically aligned rotating wheels (top wheel 220, bottom wheel 224) that are connected by a hollow cylinder (FIG. 2B, 228) that is slide-able over the center bar 240. Wheels 220, 224 further comprise a plurality of horizontally aligned cell strainers or meshes or holes (top wheel meshes 222, and bottom wheel meshes 226) that are able to allow the cells or cell mixture to de-clump and fall at an even rate downward to chamber 230.

Between the top wheel 220 and the bottom wheel 224 extends the proximal end 254 of an open-ended tube 250. Tube 250 is used in FIG. 1, step 2 to pour, or inject, a liquid comprising a fixation solution (e.g. 1-3% agarose) from the circular opening at 254 downward onto the cells on top of the bottom wheel meshes 226 as the wheel rotates.

The proximal end 254 of the tube 250 may further comprise evenly spaced holes 252 to inject the fluid downward onto the second wheel 224 at a constant rate and volume throughout the entire radius of the wheel 254 to ensure a "homogenous" mixture of cells, which then drains downward into the bottom chamber 230.

The bottom chamber 230 comprises a hollow cylinder 242 encircling the center bar 240 to enable the chamber 230 to rotate in unison (e.g. the same rate) as the bar 240 and the top and middle chambers. It also comprises a bottom surface 232 comprising a material well known in the art that is able to prevent the cell mixture from attaching to it—i.e. so that it may easily be transferred from the bottom chamber 230 into a mold (e.g. Mold A) of a pre-determined size and/or volume per the mathematical calculations disclosed supra.

Apparatus 200 may further comprise a transparent shield 260 to allow the user to view the apparatus while it is in operation, while also preventing contamination of the cells and the apparatus surfaces. In an exemplary embodiment shown in FIGS. 2A-2C, the shield 260 is hollow and cylindrically shaped. It extends from beneath the top chamber 210 downward to rest on top of the outer wall of the bottom chamber 230 (see dotted circular lines).

Step (1)—Computation of Cell Mold Volume

FIG. 1 provides a flowchart of the previously described general steps 1-6 in preparing the homogenous cell blocks using the HCM apparatus 200 of FIGS. 2A-2C. Before commencing with steps 2-6, the user must first determine the volume of the molds that the homogenous liquid cell mixture will be injected into based on the total number of affected cells, or density of the cells, desired by the user in the final cell blocks.

As illustrated in the equations infra, the total volume of the cell mold is computed from dividing the total volume of the cells that is desired in the cell blocks by user, by the percent agarose volume.

Volume of Cell Mold=Total Volume of Cells/(1-3% Agarose Volume %)

But first, the total volume of the cells is computed from the following equations. Equation "X" is an exemplification of the computation illustrated in Table 1 using 3% agarose for determining the total volume of cells X resulting from the user selecting two factors that they want in the final homogenous cell block: 1) the affected cell number or count; and 2) the ratio (in percentages) of the control (i.e. normal) cells to the affected cells.

Total Volume of Cells=4/3*pi*(Affected Cell No.)*Y

Y=[(Affected Cell Radius)$^3$+(Control Cell Radius)$^3$*(% Control/% Affected Cells)]

$$X = 4/3 * pi * (\text{Cancer Cell No.}) * \left[ \frac{\text{Cancer Cell Diameter}^3}{2} + \frac{(\text{Normal Cell Diameter})^3}{2} * \frac{\text{\% Normal Cells}}{\text{\% Cancer Cells}} \right]$$

TABLE 1

| Cancer Cell Diameter | Cancer Cell Number | Cancer Cell Percentage | Normal Cell Diameter | Percentage of Normal Cell | Total Volume of Cells | 3% Agarose Volume % | X Volume of Cell Mold μm$^3$ |
|---|---|---|---|---|---|---|---|
| 6 | 12300000 | 50% | 6.7 | 50% | 3328090574 | 97% | 110936352478 |
| 4.5 | 15300000 | 25% | 5.5 | 75% | 4728528832 | 80% | 23642644160 |
| 2 | 18300000 | 15% | 6.3 | 85% | 13653504853 | 65% | 39010013867 |

Step (2)—Pre-Treatment of Cells

Step 2 comprises the pre-treatment of the cells (control and affected) which may comprise the use of apparatus 200 of FIGS. 2A-2C, top tier 210 or all three tiers 210-230, to separate the washed cells before they are counted. Apparatus 200 is then utilized again in Step 3 to create a homogenous mixture of a liquid or a semi-solid composition that is injected into the molds where they solidify into cell blocks.

Table 2 provides a list of the sequential laboratory procedures performed when pre-treating the cells.

TABLE 2

Remove tissue culture medium and wash cells once with phosphate buffered saline (PBS).
Detach cells using trypsin and stop trypsinization by adding culture medium.
Centrifuge cells at 800 xg for 5 minutes and remove supernatant.
Wash cell pellet once with PBS.
Re-suspend the cells in 15 ml PBS.
Pass the cell suspension through a cell strainer (e.g. 70 micrometer) or through the HCM apparatus's - see FIGS. 2A-2C, 210.
Perform cell counting and cell viability using a Cellometer Auto T4 and Trypan blue staining. Ensure cell count equals user designated "affected cell number" per the equations of step 1.
Fix the cells for 24 hours at room temperature with freshly prepared 2%/4% paraformaldehyde (PFA) or 10% Neutral Buffered Formalin in PBS.

TABLE 2-continued

After fixation, centrifuge the cells at 800 xg for 5 minutes and remove the supernatant.
Rinse the cell pellet once with 70% ethanol. Keep at 4° C. until use.

Step (3)—Cell Block Preparation

Cylindrical molds of a size or volume as computed in step 1 are used for making the cell block (e.g. 4 mm in radius, 145 mm in length) (Mold A). The one time use cell block Mold A's (first mold) are kept at −10° C. for one hour before use. The cell pellet is re-suspended in phosphate buffered saline (PBS).

Because cell pellets fixed in formalin or paraformaldehyde (PFA) become very tough when the pellets are subsequently embedded into paraffin, they create a pellet with very dense cells. To prevent this, the fixed cell pellet is passed again through the apparatus 200 illustrated in FIGS. 2A-2C, which mixes the cells via circular rotation of the chambers in unison. The fixation solution (e.g. 1-3% agarose) is simultaneously added as the cells between tiers 210 and 218 to create a mixture of cells possessing a very even distribution of all cells throughout the mixture.

As shown in the Homogenous Cell Mixture (HCM) apparatus 200 of FIGS. 2A-2C, the re-suspended cells are passed through the upper chamber 210 to the middle chamber 218. The tube 250 then injects a fixation fluid simultaneously (e.g. 3% agarose) onto the rotating mixture of cells. The cell/agarose mixture then flows through the plurality of holes in the middle chamber lower wheel 224 and into the lower collection chamber 230.

The cell/agarose mixture is then injected (e.g. pumped by means well known in the art), or poured from detachable chamber 230, into the prepared Mold A, which is subsequently kept at −10° C. for 5 minutes. The solid composition or semi-solid composition (i.e. cell block) is then removed from the Mold A and put into individual 50 ml tubes containing 70% ethanol. The cell blocks are processed for paraffin on individual 50 ml tubes using the sequential steps listed in the table of FIG. 3 comprising the cell block paraffin processing schedule.

Immediately after paraffin processing, individual blocks are removed from the paraffin and embedded onto a paraffin Mold B (e.g. 2 cm*2 cm*2 cm) (second mold). The cell blocks are wrapped with parafilm and kept in air-tight box at 4° C. until sectioning.

Step (4)—Sectioning Cell Blocks and Hematoxylin Staining

The cell blocks from Mold B are removed from the 4° C. refrigerator and mounted onto cassettes for sectioning utilizing a Leica microtome. A single-use high profile microtome blade is used for the sectioning of each cell block. A plurality of FFPE Sections of 10 μm thickness are cut along the cross-section from each block. The sections are mounted onto positively charged glass slides and left for air drying at room temperature for 30 minutes. The slides are then baked in a 56° C. oven for 20 minutes before hematoxylin staining using the procedure of sequential laboratory steps that are shown in the table of FIG. 4.

Although the present invention is for preparing 10 μm FFPE sections of homogenous cell blocks, it is noted that one of skill in the art would readily know how to adjust this disclosure for producing other types of homogenous cell blocks, such as 5 μm FFPE sections and non-FFPE cell blocks.

Step (5)—DNA/RNA Extraction

To confirm homogeneity of the cell blocks, multiple sections (e.g. 1000 cross-sections) are cut from a cell block containing millions of cells, and DNA or RNA extraction is performed on selected individual sections (e.g. every 100th section) as per FIG. 1, step 5, and then the DNA or RNA is quantified as per FIG. 1, step 6. Additionally, digital microscopy images taken of the hematoxylin-stained cell sections demonstrate that the cells are scattered evenly throughout the cell block section.

DNA and RNA extraction methods are well known in the art. By way of exemplification, DNA extraction is performed using the Qiagen® DNeasy Blood & Tissue Kit (cat. #69504, Qiagen®, USA) according to the manufacturer's protocol with two exceptions: 1) Proteinase K digestion is performed overnight in a 56° C. water bath; and 2) DNA is eluted with 100 μl elution buffer twice to yield a total volume of 200 μl DNA.

And by way of exemplification, RNA extraction from the cell block sections is achieved using Qiagen® RNeasy FFPE RNA extraction kit. The quantity of RNA is perfectly consistent using each section cut from the block with the same thickness, which indicates that the cell block is in a perfect homogeneous stage.

Step (6)—DNA/RNA Quantification

DNA and RNA quantification methods are well known in the art. By way of exemplification, the DNA is quantified using a Quant-iT PicoGreen® dsDNA Reagent and Kit (Molecular Probes, Eugene, Oreg.) or Quant-iT RiboGreen® RNA Reagent and Kit. Standard curve samples are freshly diluted from the Lambda DNA standard before each batch of sample measurements. DNA measurement of unknown samples are performed according to the manufacturer's recommendation. Fluorescence readings are taken with a TBS-380 Mini-Fluorometer® (Turner Biosystems, Sunnyvale, Calif.) using 10×10 mm square polystyrene disposable cuvettes. Sample DNA concentrations are then extrapolated from the Lambda DNA standard curve.

RNA is quantified using the RiboGreen® RNA quantitation reagent. In the high-range assay, the RiboGreen® reagent is diluted 200-fold into 10 mM Tris-HCl, 1 mM EDTA, pH 7.5 (TE). Then 100 μL of the reagent solution is added to microplate wells containing 100 μL ribosomal RNA in TE. Using the low-range assay, the RiboGreen® reagent is diluted 2000-fold into TE, and 100 μL of the reagent solution is added to 100 μL of ribosomal RNA in TE. The RNA samples are excited at 485±10 nm, and the fluorescence emission intensity is measured at 530±12.5 nm using a fluorescence microplate reader. Sample RNA concentration are then extrapolated using the Ribosomal RNA standard curve well known in the art.

EXEMPLIFICATIONS

Figure 5:
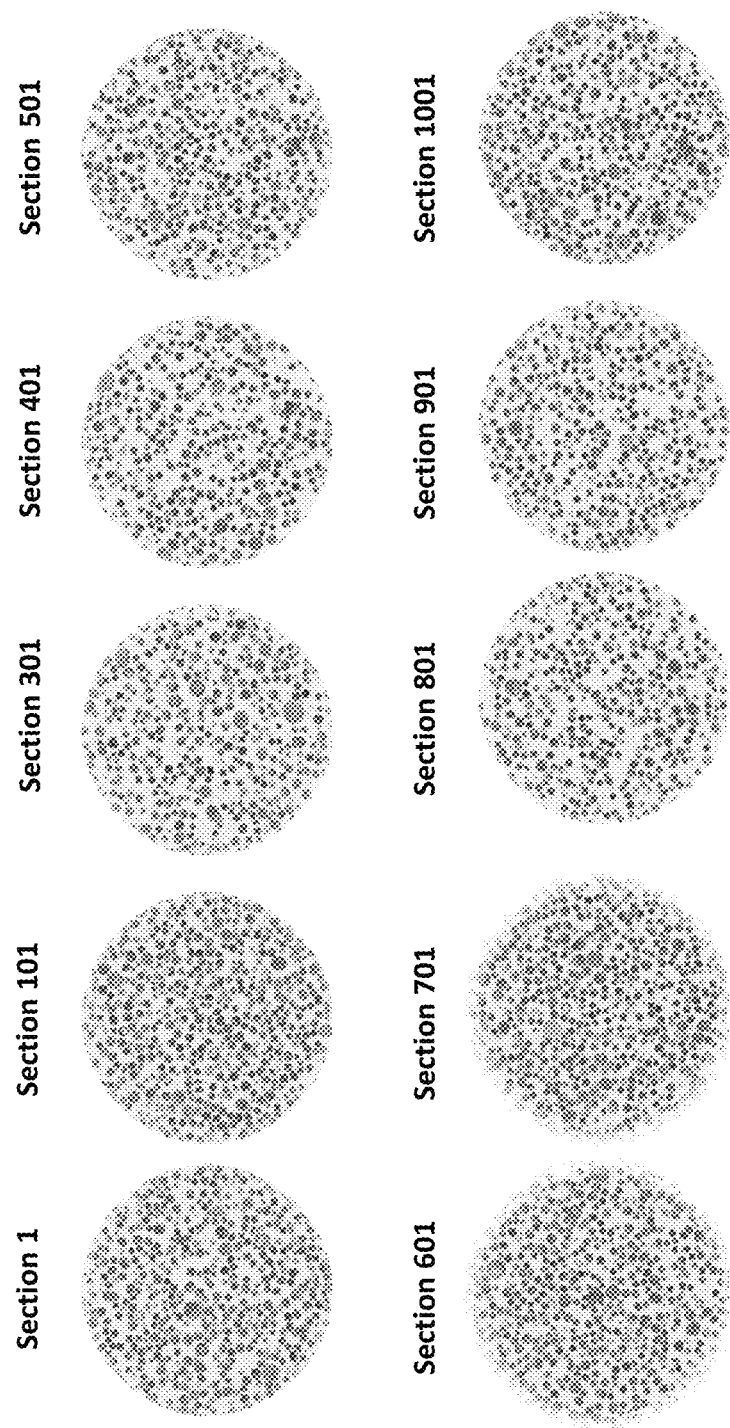
FIG. 5 illustrates a plurality of digital images of sections sequentially cut from a homogenous cell block stained for DNA.

FIG. 5 comprises digital microscopy images taken of the DNA hematoxylin-stained cells in the FFPE slices with 5 μm thickness cut from an in vitro homogenous cell block comprising HCT-116 cells. The results of the DNA quantification for each slice are shown in FIG. 7A.

Figure 6:
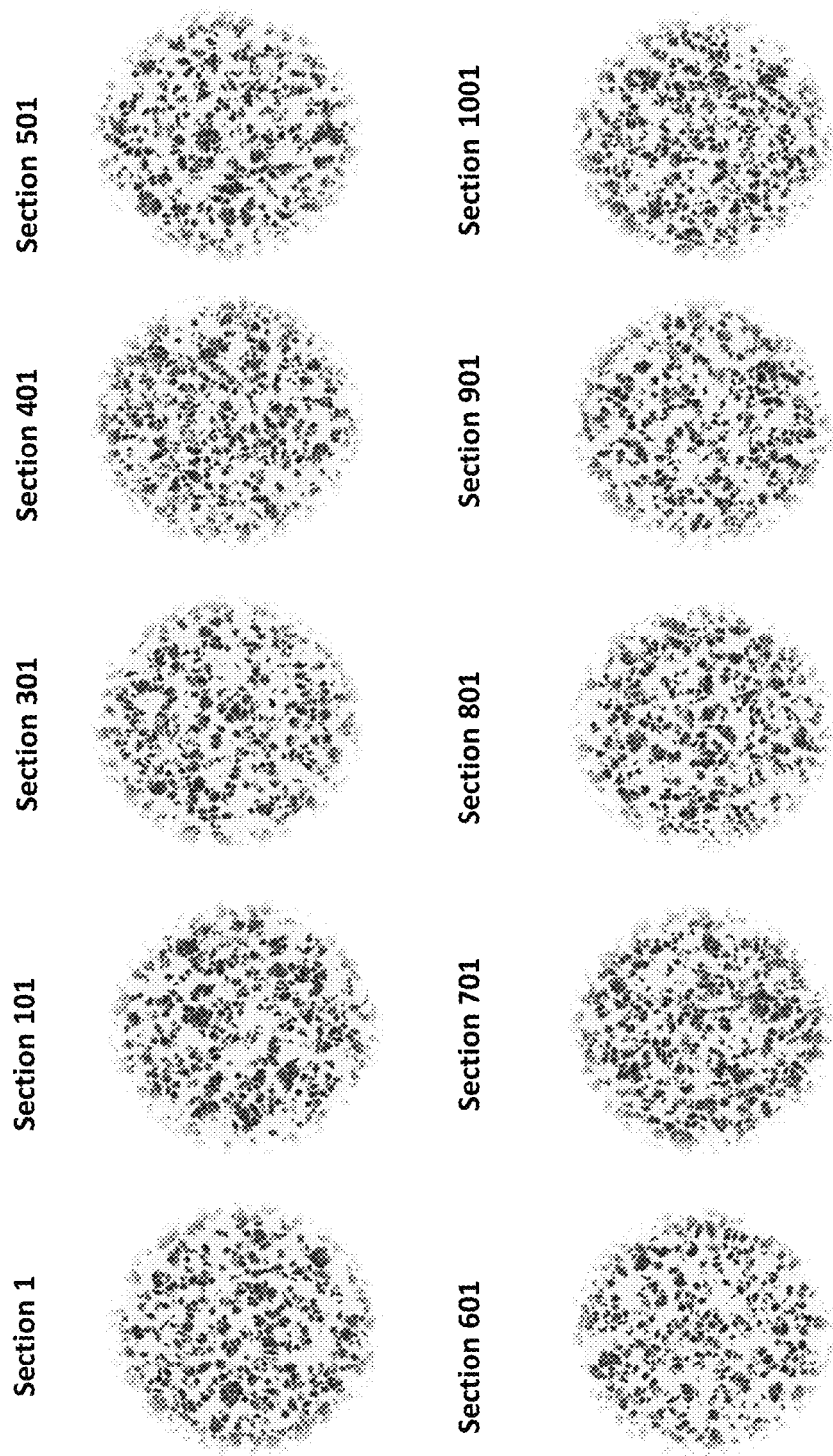
FIG. 6 illustrates a plurality of digital images of sections sequentially cut from another homogenous cell block stained for RNA.

FIG. 6 comprises digital microscopy images taken of the RNA hematoxylin-stained cells in the FFPE slices with 5 μm thickness cut from a different cell block than FIG. 5. The results of the RNA quantification for each slice are shown in FIG. 7B.

Both cell blocks were produced by the method of the present invention FIGS. 1, 3 and 4 and by using the multi-chambered-tiered apparatus of FIGS. 2A-C.

As illustrated in the table of FIG. 7A, the total number of cells, affected and normal, and the amount of DNA was quantified in each of eleven sections-slices: 1, 101, 201, 301, 401, 501, 601, 701, 801, 901, and 1001. Of the eleven slices analyzed, the highest number of cells was in slice 801 with 845 cells and with a total DNA of 4.47 ng; while the lowest number of cells was in slice 1001 with a cell count of 815 and a total amount of DNA 4.02 ng. The small range of total cell count between the eleven slices (815-845), and the small range of the amount of DNA between the eleven slices (4.02-4.47 ng), demonstrates the homogenous nature of the cell block.

Likewise, as illustrated in the table of FIG. 7B, the total number of cells, affected and normal, and the amount of RNA was quantified in each of eleven sections-slices: 1, 101, 201, 301, 401, 501, 601, 701, 801, 901, and 1001. Of the eleven slices analyzed, the highest number of cells was in slice 101 with 1089 cells and with a total RNA of 21.2 ng; while the lowest number of cell was in slice 1 with a cell count of 1002 and a total amount of RNA 19.8 ng. The small range of total cell count between the eleven slices (1002-1089), and the small range of the amount of RNA between the eleven slices (19.8-21.2 ng), demonstrates the homogenous nature of the cell block.

While the present invention has been described with reference to a few specific embodiments, the description is illustrative of the invention and is not to be construed as limiting the invention. Various modifications may occur to those skilled in the art without departing from the true spirit and scope of the invention as defined by the appended claims.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

It is to be understood that the phraseology and terminology employed herein is not to be construed as limiting and are for descriptive purpose only.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including", "comprising", "consisting" and grammatical variants thereof do not preclude the addition of one or more components, features, steps, or integers or groups thereof and that the terms are to be construed as specifying components, features, steps or integers.

What is claimed is:

1. A multi-chambered-tiered apparatus comprising,
    a. a rotating circular upper cell containing chamber (FIG. 2A, item 210) able to pass the pre-treated cells downward onto a circular rotating middle chamber, wherein the chamber is detachable from the apparatus;
    b. a circular rotating middle chamber comprising an upper wheel (FIG. 2A, item 220) and a lower wheel (FIG. 2A, item 224) able to pass the pre-treated cells downward through to a rotating lower cell collection chamber (FIG. 2A, item 230), and an open-ended tube (FIG. 2A, item 250) able to simultaneously inject the fluid to create a homogenous cell mixture; and
    c. a rotating lower cell collection chamber (FIG. 2A, item 230) positioned to receive the homogenous cell mixture from the rotating middle secondary chamber; and
    d. a motorized mechanism to rotate the upper, middle, and lower chambers in unison (FIG. 2A, items 270, 272, 274).

2. The multi-chambered-tiered apparatus of claim 1, wherein the open-ended tube is positioned between the upper chamber and the lower chamber, and is able to inject liquid comprising a fixation of a specific volume that is determined by the type of cells.

3. The multi-chambered-tiered apparatus of claim 2, wherein the open end of the tube further comprises a plurality of holes evenly spaced (FIG. 2A, 252) to inject the fluid in a pattern of even distribution.

4. The multi-chambered-tiered apparatus of claim 1, wherein the apparatus further comprises a transparent, hollow cylinder positioned to encase the middle and lower chambers and an open-ended tube proximal end in order to prevent contamination of the pre-treated cells within the apparatus.

5. A method of making an in vitro solid composition comprising a homogenous mixture of cells evenly distributed throughout the composition for use as an experimental positive control, the steps comprising,
    a. passing a plurality of pre-treated cells vertically through holes in a multi-chambered-tiered apparatus and mixing the pre-treated cells with a fluid simultaneously to create a homogenous cell mixture of immobilized cells, wherein the multi-chambered-tiered apparatus comprises,
        a rotating circular upper cell containing chamber (FIG. 2A, item 210) able to pass the pre-treated cells downward onto a circular rotating middle chamber;
        a circular rotating middle chamber comprising an upper wheel (FIG. 2A, item 220) and a lower wheel (FIG. 2A, item 224) able to pass the pre-treated cells downward through to a rotating lower cell collection chamber (FIG. 2A, item 230);
        a rotating lower cell collection chamber (FIG. 2A, item 230) positioned to receive the homogenous cell mixture from the rotating middle secondary chamber;
        an open-ended tube (FIG. 2A, item 250) situated between the upper and lower wheel, and able to inject a fluid onto the lower wheel to create a homogenous cell mixture;
        a motorized mechanism to rotate the upper, middle, and lower chambers in unison (FIG. 2A, items 270, 272, 274);
    b. injecting the homogenous cell mixture into a first mold, letting the mixture set to immobilize the cell mixture, and removing a solid composition from the first mold;

c. processing the solid composition with paraffin, removing the solid composition from the paraffin, and embedding the solid composition into a second mold to produce formalin fixed paraffin embedded (FFPE) cells; and, d. removing the solid composition from the second mold, wherein the solid composition comprises a homogenous mixture of formalin fixed paraffin embedded (FFPE) cells with a uniform density of cells throughout the solid composition.

6. The method of claim 5, wherein steps (a-d) are preceded by selecting a one or more cell types, and a desired total cell number of the selected cells in the solid composition, and determining the volume of the first and second mold based on the diameter or radius of the selected cell types, and the total cell number.

7. The method of claim 5, wherein the mixture of cells comprises one or more of: a pre-determined ratio of different types of cells; different combination of certain percentages of each cell type; the same type of cells exposed to different treatment protocols; and, wherein the ratio of the mixture of cells is evenly distributed within the composition.

8. The method of claim 5, wherein the mixture of cells comprises one or more of: the same type of cells with different genetic modifications; the same type of cells with different protein or nucleic acids expression; different types of cells with different genetic backgrounds; and, different types of cells with different gene/protein expression levels.

9. The method of claim 5, wherein the open-ended tube is positioned between the upper chamber and the lower chamber to inject liquid comprising a fixation solution of a specific volume that is determined by the type of cells.

10. The method of claim 9, wherein the liquid comprises a 3% agarose fixation solution.

11. The method of claim 5, wherein the open end of the tube further comprises a plurality of holes evenly spaced (FIG. 2A, 252) to inject the fluid in a pattern of even distribution.

12. The method of claim 5, wherein the pre-treated cells passed through the apparatus are in suspension, a fixed pellet, or an unfixed pellet form.

13. The method of claim 5, wherein pre-treating cells comprises the steps of, fixing the cells in paraformaldehyde or formaldehyde and phosphate buffered saline (PBS), then centrifuging and rinsing the cells.

14. The method of claim 13, wherein the pre-treatment of cells further comprises:
 a) fixing the cells for 24 hours at room temperature with freshly prepared 2% paraformaldehyde in PBS to create a cell pellet;
 b) centrifuging the cell pellet;
 c) rinsing the cell pellet with 70% ethanol; and,
 d) storing the cells at 4 degrees Celsius.

15. The method of claim 5, further comprising sectioning the solid composition of the homogenous mixture of FFPE cells into 5 or 10 µm sections, baking at 56 degrees Celsius for 20 minutes, and staining with hematoxylin.

16. The method of claim 15, further comprising confirming that the solid composition is a homogenous mixture of FFPE cells via DNA or RNA extraction, and via DNA or RNA quantification of multiple sections of the solid composition.

17. A standard comprising a homogenous mixture of cells within a formalin fixed paraffin embedded tissue block evenly distributed throughout a solid composition with a uniform distribution and density of the cells, without or with minimal cell clumping, of a same cell type, or of a ratio of different cell types, within the mixture of cells, the standard produced by the steps comprising, a. passing a plurality of pre-treated cells vertically through holes in a multi-chambered-tiered apparatus and mixing the pre-treated cells with a fluid simultaneously to create a homogenous cell mixture of immobilized cells, wherein the multi-chambered-tiered apparatus comprises,
 a rotating circular upper cell containing chamber (FIG. 2A, item 210) able to pass the pre-treated cells downward onto a circular rotating middle secondary chamber, wherein a bottom of the upper chamber comprises a plurality of evenly spaced holes (FIG. 2B, item 212) that are sized to permit single cells of a specific diameter to fall downward through to prevent cell clumping;
 a circular rotating middle chamber comprising an upper wheel (FIG. 2A, item 220) and a lower wheel (FIG. 2A, item 224) that each comprise a plurality of mesh sections (FIG. 2A, item 222, 226) able to pass the pre-treated cells at an even rate, and de-clumped, downward through to a lower cell collection chamber (FIG. 2A, item 230), and an open-ended tube (FIG. 2A, item 250) able to simultaneously inject the fluid to create a homogenous cell mixture;
 a rotating lower cell collection chamber (FIG. 2A, item 230) positioned to receive the homogenous cell mixture from the rotating middle secondary chamber;
 a motorized mechanism to rotate the upper, middle, and lower chambers in unison (FIG. 2A, items 270, 272, 274);

b. injecting the homogenous cell mixture into a first mold, letting the mixture set to immobilize the cell mixture, and removing a solid composition from the first mold;

c. processing the solid composition with paraffin, removing the solid composition from the paraffin, and embedding the solid composition into a second mold to produce formalin fixed paraffin embedded (FFPE) cells;

d. removing the solid composition from the second mold, wherein the solid composition comprises a homogenous mixture of formalin fixed paraffin embedded (FFPE) cells with a uniform density of cells throughout the solid composition; and e. wherein solid composition is suitable for use as: a biomarker standard for any tissue based biomarker study; a biomarker analysis that uses techniques comprising polymerase chain reaction (PCR), DNA/protein sequencing, and microarrays; and a standard for sensitivity and specificity evaluation histology based biomarker studies conducted using machines or manual operation methods.

18. The standard of claim 17, wherein the solid composition comprises one or more cell types, and a desired density range of the cells, and wherein the volume of the first mold and second mold is able to be based on the diameter of the cell types, and the desired density.

19. The standard of claim 17, wherein the mixture of cells comprises: a pre-determined ratio of different types of cells; a different combination of certain percentages of each cell type; and/or the same type of cells exposed to different treatment protocols; and, wherein the ratio of the mixture of cells is evenly distributed within the composition.

20. The standard of claim 17, wherein the mixture of cells comprises: a same type of cells with different genetic modifications; a same type of cells with different protein or nucleic acids expression; different types of cells with different genetic backgrounds; and/or, different types of cells with different gene/protein expression levels.

* * * * *